United States Patent [19]
Brodin et al.

[11] Patent Number: 6,031,007
[45] Date of Patent: Feb. 29, 2000

[54] PHARMACEUTICAL COMPOSITION WITH ANAESTHETIC EFFECT

[75] Inventors: Arne Brodin, Södertälje, Sweden; Raymond Fynes, Mississauga, Canada; Lars Heijl, Lerum, Sweden; Adela Nyqvist-Mayer, Tullinge, Sweden; Marie Scherlund, Bromma, Sweden

[73] Assignee: Astra AB, Sweden

[21] Appl. No.: 08/875,888

[22] PCT Filed: Apr. 1, 1997

[86] PCT No.: PCT/SE97/00566

§ 371 Date: Aug. 6, 1997

§ 102(e) Date: Aug. 6, 1997

[87] PCT Pub. No.: WO97/38675

PCT Pub. Date: Oct. 23, 1997

[30] Foreign Application Priority Data

Apr. 12, 1996 [SE] Sweden ................................ 9601421

[51] Int. Cl.⁷ .......................................... A61K 9/06
[52] U.S. Cl. .................. 514/716; 514/626; 514/772; 514/817; 514/818; 514/900
[58] Field of Search ................... 514/626, 716, 514/772, 817, 818, 900

[56] References Cited

U.S. PATENT DOCUMENTS

| | | | |
|---|---|---|---|
| 4,188,373 | 2/1980 | Krezanoski | 424/78 |
| 4,478,822 | 10/1984 | Haslam et al. | 424/78 |
| 4,780,320 | 10/1988 | Baker . | |
| 5,114,719 | 5/1992 | Sabel et al. | 424/422 |
| 5,288,497 | 2/1994 | Stanley et al. | 424/440 |
| 5,288,498 | 2/1994 | Stanley et al. | 424/440 |
| 5,292,516 | 3/1994 | Veigas et al. | 424/423 |
| 5,589,180 | 12/1996 | Hind | 424/402 |
| 5,612,052 | 3/1997 | Shalaby | 424/426 |
| 5,635,540 | 6/1997 | Edlich et al. | 514/772.3 |

FOREIGN PATENT DOCUMENTS

| | | | |
|---|---|---|---|
| 241178 | 10/1987 | European Pat. Off. | A61K 9/70 |
| 455396 | 11/1991 | European Pat. Off. | A61K 9/06 |
| 2 704 429 | 11/1994 | France . | |

OTHER PUBLICATIONS

CA 123:152960, Shike et al, Jun. 20, 1995.
WPIDS AN 94–351141 Balard et al, Nov. 4, 1994.
CA 105:11993, Nyqvist–Mayer et al, 1986.
Nyqvist–Mayer et al, J Pharmaceutical Sciences, 75(4) pp. 365–373, Apr. 1986.

*Primary Examiner*—Rebecca Cook
*Attorney, Agent, or Firm*—Michael A. Sanzo; Vinson & Elkins L.L.P.

[57] ABSTRACT

The invention is directed to a novel pharmaceutical composition comprising one or more local anaesthetics in oil form, one or more surfactants, water and optionally a taste masking agent. The novel composition is advantageously used as a local anaesthetic for pain relief within the oral cavity.

17 Claims, No Drawings

PHARMACEUTICAL COMPOSITION WITH ANAESTHETIC EFFECT

This is a 371 of PCT/SE97/00566 filed Apr. 1, 1997.

THE FIELD OF THE INVENTION

The present invention is directed to a new pharmaceutical composition and its use in therapy, particularly as an anaesthetic for use on mucous membranes and particularly within the oral cavity.

BACKGROUND AND PRIOR ART

It is estimated that approximately 10–13% of the population suffers from periodontal diseases with pathological periodontal pockets. In order to eliminate or control the disease and arrest further periodontal tissue destruction, periodontal pockets need repeated subgingival mechanical debridement/cleansing. The number of periodontal pockets in a patient may vary as can the pocket depth measurement. Approximately 40% of all periodontal scaling procedures performed involve some kind of anaesthesia.

Accumulation of bacterial plaque on teeth and in the gingival sulcus elicits an inflammatory response in the marginal gingiva which may spread in an apical direction and result in loss of tooth support with the formation of periodontal pockets. The object of mechanical debridement of periodontal pockets is to control and arrest further destruction of tooth support by removal of plaque and calculus from within the pockets.

The majority of the scaling procedures are performed by hygienists. The main use of anaesthesia techniques used in conjunction with periodontal scaling is either a nerve block or infiltration. Infiltration anaesthesia is either carried out alone or in combination with topical anaesthesia, mainly jelly, ointment or spray. However, the problem with existing topical products are lack of efficacy due to inadequate depth of penetration, too short duration and difficulties in administration due to spread, taste etc. EP 244 118 discloses a controlled release drug delivery system for placement in the periodontal pocket, having a plurality of discrete microparticles consisting of a rate-controlling polymer matrix having a drug dispersed therein, said microparticles being in the range of 10–500 $\mu$m. EP 241 178 also discloses a controlled release drug delivery system for placement in the periodontal pocket, which composition comprises solid particles having an average size of 1–500 $\mu$m. However, the drug delivery systems disclosed in both these prior art patents are deviced for administration of a medicament for a longer period of time. Thus the drug delivery systems of EP 244 118 and EP 241 178 are not suitable for use in pain management in conjunction with minor surgical procedures, where a fast onset of action and relatively short duration is required.

Thus, the problem underlying the present invention is to provide a pharmaceutical composition which would provide effective pain relief in conjunction with periodontal scaling and root planing following local administration. In other words, the object of the invention is to provide a local anaesthetic that can be applied in a facile manner in the oral cavity, and more precisely within periodontal pockets. A further object of the invention is to provide a pharmaceutical composition having a short onset time and an adequate duration for the intended procedure, with no inconvenient anaesthesia.

OUTLINE OF THE INVENTION

The problem identified above has now been solved by providing a new pharmaceutical composition which preferably is in form of an emulsion, more preferably in form of a microemulsion, comprising the following ingredients:

(i) One or more local anaesthetics in oil form in the final composition;

(ii) one or more surfactants, together present in an amount effective to produce a homogenous formulation; and (iii) water up to 100% by weight, based on the total weight of the composition.

The local anaesthetic in the final composition is one or more local anaesthetics in oil form as such, or a eutectic mixture formed by two or more local anaesthetics. The amount of the local anaesthetic in the oil phase depends on the pH-value of the formulation.

In a particularly preferred embodiment of the invention the local anaesthetic is a eutectic mixture of lidocaine base and prilocaine base.

In a further embodiment of the invention a eutectic mixture may also be formed by two or more substances, where at least one of these substances is a local anaesthetic.

The amount of the local anaesthetic or mixture of local anaesthetics is preferably in the range 0.5–20% by weight, more preferably in the range 2–7% by weight, based on the total weight of the composition.

The local anaesthetic(s) in the final composition are present in a non-solid form.

By the wording "surfactant" we mean any agent that acts as a solubilizer and/or as an emulsifier and/or as a thickening agent with thermoreversible gelling properties. The wording surfactant is also intended to include thickening agents without thermoreversible properties. If only one surfactant is used in the composition, it must be selected with care and in suitable amounts so that it acts both as a solubilizer and/or as an emulsifier, as well as a thickening agent with thermoreversible gelling properties. If more than one surfactant is present in the composition, at least one of the surfactants should have thermoreversible gelling properties. The total amount of the surfactant(s) should be present in an amount effective to produce a homogenous formulation.

The surfactants are preferably selected from non-ionic surfactants, more preferably from any non-ionic poloxamer known in the art.

Poloxamers are synthetic block copolymers of hydrophilic ethylene oxide chains and hydrophobic propylene oxide chains, having the general formula HO—$[C_2H_4O]_a$—$[C_3H_6O]_b$—$[C_2H_4O]_a$—H, a and b representing the number of the hydrophilic and hydrophobic chains respectively.

By choosing the surfactant(s) having hydrophobic and hydrophilic domains in appropriate amounts, in combination with an appropriate amount of the local anaesthetic or mixture of local anaesthetics, it is possible to achieve a composition having suitable thermoreversible gelling properties, i.e. the system remains less viscous at room temperature, and upon application into a periodontal pocket the viscosity of the composition is increased. In other words, the pharmaceutical composition according to the present invention is less viscous at room temperature. Above this temperature the composition is more viscous, providing the advantage of remaining in the periodontal pockets for the time necessary to induce local anaesthesia. The change in viscosity is reversible with temperature.

In a particularly preferred embodiment of the invention the surfactant is one or more of Lutrol F68®, which also has the name poloxamer 188 and wherein a=80 and b=27, and Lutrol F127®, which also has the name poloxamer 407 and wherein a=101 and b=56, the definitions being in accordance with USP (1995) NF18, p. 2279. Lutrol F68® and Lutrol F127® are commercially available from BASF.

In a further preferred embodiment of the invention the surfactant Arlatone 289® is used, which also has the name polyoxyethylene hydrogenated castor oil, as well as Adinol CT95® which is sodium N-methyl N-cocoyl taurate.

The total amount of surfactant(s) is preferably present in an amount of up to 50% by weight, based on the total weight of the composition.

The pH-value of the pharmaceutical composition is adjusted with suitable acid or base in such a way that the final pH-value for the composition is:

(A) $pH \geq [pK_a \text{ (local anaesthetic)}] - 1.0$ if the composition comprises one local anaesthetic; or (B) $pH \geq [pK_a \text{ (local anaesthetic with the lowest } pK_a \text{ value)}] - 1.0$ if the composition comprises two or more local anaesthetics.

Preferably the pH is over 7.5.

Since local anaesthetics by nature have an unpleasant bitter taste, one or more taste masking agents may optionally be added to the pharmaceutical composition. The choice of taste masking agents will be appreciated by a person skilled in the art, but as an example any fruit flavours may be mentioned.

By topical application within the periodontal pocket, local anaesthesia is achieved in a very localised area, without causing the often extensive soft tissues such as the tongue, cheek and lips, to get anaesthetized which is often the case with infiltration anaesthesia. Preferably the composition is applied into a periodontal pocket by means of a blunt needle, thereby facilitating the administration of the anaesthetic and giving an increased patient comfort.

The pharmaceutical composition of the present invention has a fast onset of action being from seconds and up to approximately 5–15 minutes. The onset time is most preferably from seconds and up to approximately 5 minutes.

For the definition of emulsions, we refer to *Pharmaceutics, The Science of Dosage Form Design*, 1988, p. 109–110, by ME Aulton.

The pharmaceutical composition according to the present invention is preferably a microemulsion. By microemulsion we mean a formulation that consists of water, oil and amphiphile(s) which constitute a single optically isotropic and thermodynamically stable liquid solution (I. Danielsson and B Lindman, *Colloids Surf*. 3:391, (1981)). This provides a suitable amount of the local anaesthetic in the oil phase, which in turn confers a fast onset of action. No separate oil needs to be added to the composition, since the oil is already present by the active component(s) as such. A further advantage is that a thermodynamically stable composition is achieved in a temperature range of 5–40° C.

The pharmaceutical composition according to the present invention may advantageously also be used as a local anaesthetic on other surfaces and/or cavities than in the oral cavity. The composition may thus also be used vaginally, genitally and rectally.

The local anaesthetic(s) used for preparing a pharmaceutical composition according to the present invention may be selected from any local anaesthetic. Preferably the local anaesthetic as the starting material is in a non-ionized form.

In the final composition a fraction of the local anaesthetic or mixture of local anaesthetics are present in oil form. The size of this fraction, local anaesthetics in oil form, depends on the pH of the composition.

The best mode of performing the invention known at present, is to use the composition according to Example 1.

Methods of Preparation

The pharmaceutical composition according to the present invention may be prepared by the following steps:

(i) the local anaesthetic(s) and the surfactant with the lowest molecular weight if more than one surfactant is used, are melted together;

(ii) a part of the water is slowly added to the melt (i) during homogenization, forming an emulsion concentrate;

(iii) if more than one surfactant is used, the surfactant with the higher molecular weight is dispersed in water;

(iv) the emulsion concentrate of step (ii) and part of the surfactant solution of step (iii) are thoroughly mixed;

(v) the pH-value is adjusted by the addition of a suitable acid or base;

(vi) the weight is adjusted with water to the final weight of the composition.

The composition is preferably kept at 5° C. until a homogenous composition is obtained.

DETAILED DESCRIPTION OF THE INVENTION

The invention will now be described in more detail by the following examples, which are not to be construed as limiting the invention.

| Example 1 | [% by weight] |
|---|---|
| Lidocaine | 2.50 |
| Prilocaine | 2.50 |
| Lutrol F68 ® | 5.50 |
| Lutrol F127 ® | 15.50 |
| purified water up to a total weight of 100%. | |

The composition was prepared by following the procedure described above, and the pH-value was adjusted by adding 2 M hydrochloric acid.

| Example 2 | [% by weight] |
|---|---|
| Lidocaine | 2.50 |
| Prilocaine | 2.50 |
| Lutrol F68 ® | 5.00 |
| Lutrol F127 ® | 16.25 |
| purified water up to a total weight of 100%. | |

The composition was prepared by following the procedure described above, and the pH-value was adjusted by adding 2 M hydrochloric acid.

| Example 3 | [% by weight] |
|---|---|
| Lidocaine | 2.25 |
| Prilocaine | 2.25 |
| Lutrol F68 ® | 3.5 |
| Lutrol F127 ® | 14.0 |
| purified water up to a total weight of 100%. | |

The composition was prepared by following the procedure described above, and the pH-value was adjusted by adding 2 M hydrochloric acid.

| Example 4 | [% by weight] |
|---|---|
| Lidocaine | 2.25 |
| Prilocaine | 2.25 |
| Arlatone 289 ® | 1.90 |
| Adinol CT95 ® | 0.07 |
| Lutrol F127 | 14.00 |
| purified water up to a total weight of 100%. | |

The composition was prepared by following the procedure described above, and the pH-value was adjusted by adding 2 M hydrochloric acid.

| Example 5 | [% by weight] |
|---|---|
| Lidocaine | 2.25 |
| Prilocaine | 2.25 |
| Arlatone 289 ® | 1.90 |
| Adinol CT95 ® | 0.16 |
| Lutrol F127 | 14.00 |
| purified water up to a total weight of 100%. | |

The composition was prepared by following the procedure described above, and the pH-value was adjusted by adding 2 M hydrochloric acid.

| Example 6 | [% by weight] |
|---|---|
| Lidocaine | 2.25 |
| Prilocaine | 2.25 |
| Arlatone 289 ® | 1.90 |
| Adinol CT95 ® | 0.28 |
| Lutrol F127 | 14.00 |
| purified water up to a total weight of 100%. | |

The composition was prepared by following the procedure described above, and the pH-value was adjusted by adding 2 M hydrochloric acid.

EXAMPLE 7 AND 8

In Examples 7 and 8, a local anaesthetic of the formula (I) was used as the acive ingredient.

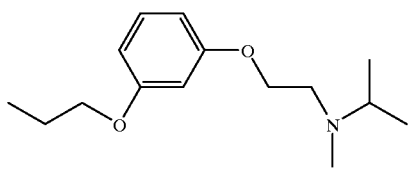

(I)

This compound is disclosed in the International Patent Application PCT/SE96/01361.

The following pharmaceutical compositions were prepared.

| Example 7 | [% by weight] |
|---|---|
| Compound (I) | 2.5 |
| Lutrol F127 ® | 17.0 |
| Lutrol F68 ® | 5.5 |
| purified water up to a total weight of 100%. | |

The composition was prepared by following the procedure described above, and the pH-value was adjusted by adding 2 M hydrochloric acid.

| Example 8 | [% by weight] |
|---|---|
| Compound (I) | 2.5 |
| Lutrol F127 ® | 20.0 |
| Lutrol F68 ® | 5.5 |
| purified water up to a total weight of 100%. | |

The composition was prepared by following the procedure described above, and the pH-value was adjusted by adding 2 M hydrochloric acid.

BIOLOGICAL STUDIES

A pharmaceutical composition according to Example 1 was applied to a human periodontal pocket with a blunt end needle. After an onset time of 30–45 seconds, a satisfactory anaesthetic effect had been achieved in order that periodontal scaling could be performed. The scaling was initiated, and the time taken to scale the tooth was noted. At the end of the scaling, the intensity of pain was measured by means of a visual analogue scale (VAS). The duration of the anaesthetic effect was 10–20 minutes.

We claim:

1. The pharmaceutical composition comprising:
   (i) one or more local anaesthetics in oil form;
   (ii) one or more surfactants in an amount effective to produce a homogenous formulation wherein, at least one surfactant has thermoreversible gelling properties; and
   (iii) water;
   wherein said composition is in the form of an emulsion or microemulsion and has thermoreversible gelling properties such that said composition is less viscous at room temperature than after introduction onto a mucous membrane of a patient.

2. The pharmaceutical composition according to claim 1, further comprising one or more taste masking agents.

3. The pharmaceutical composition according to claim 1, wherein said one or more local anaesthetics are present in an amount of 0.5–20% by weight based on the total weight of the composition.

4. The pharmaceutical composition according to claim 3, wherein said one or more local anaesthetics are present in an amount of 2–7% by weight based on the total weight of the composition.

5. The pharmaceutical composition according to claim 1, wherein said one or more local anaesthetics is a eutectic mixture of local anaesthetics.

6. The pharmaceutical composition according to claim 5, wherein said one or more local anaesthetics is a eutectic mixture of lidocaine and prilocaine.

7. The pharmaceutical composition according to claim 1, wherein said one or more local anaesthetics comprises

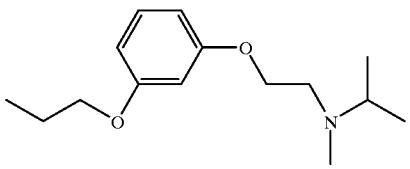
(I)

8. The pharmaceutical composition according to any one of claims 1–7, comprising more than one surfactant of which at least one is a surfactant having thermoreversible gelling properties.

9. The pharmaceutical composition according to any one of claims 1–7, wherein the total amount of surfactant is present in an amount of up to 50% by weight based on the total weight of the composition.

10. The pharmaceutical composition according to any one of claims 1–7, wherein the surfactant is a non-ionic surfactant.

11. The pharmaceutical composition according to claim 10, wherein the surfactant is a poloxamer.

12. The pharmaceutical composition according to any one of claims 1–7, comprising the two surfactants Poloxamer 188® and Poloxamer 407®.

13. The method of treating a patient for pain associated with periodontal scaling, comprising applying to the periodontal pocket of said patient an effective amount of the pharmaceutical composition according to claim 1.

14. The process for the manufacture of the pharmaceutical composition according to claim 1, wherein said composition has more than one surfactant, comprising:

(a) melting together said one or more local anesthetics and the surfactant with the lowest molecular weight;

(b) adding water to the melt of step (a) during homogenization to form an emulsion concentrate;

(c) dispersing the remaining surfactant or surfactants in water;

(d) mixing, the emulsion concentrate of step (b) and the surfactant solution of step (c);

(e) adjusting the pH of the mixture of step (d) so that the final pH is greater than or equal to $pK_a-1$, wherein $pK_a$ is that of the local anesthetic with the lowest $pK_a$; and (f) adding water to the final weight of the composition.

15. A process for the manufacture of the pharmaceutical composition according to claim 1, wherein said composition has only one surfactant, comprising:

(a) melting together said one or more local anesthetics and said surfactant;

(b) addingc water to the melt of step (a) during homogenization to form an emulsion concentrate;

(c) adjusting the pH of the mixture of step (b) so that the final pH is greater than or equal to $pK_a-1$, wherein $pK_a$ is that of the local anesthetic with the lowest $pK_a$; and (d) adding water to the final weight of the composition.

16. The composition of claim 1, wherein said one or more local anesthetics comprise 0.5 to 20% of the final weight of said composition, and said one or more surfactants comprise up to 50% of the final weight of said composition.

17. The composition of claim 16 wherein the pH of said composition is greater than or equal to $pK_a-1$, wherein $pK_a$ is that of the local anesthetic with the lowest $pK_a$.

* * * * *